United States Patent [19]
Glazer et al.

[11] Patent Number: 6,054,272
[45] Date of Patent: *Apr. 25, 2000

[54] DYES DESIGNED FOR HIGH SENSITIVITY DETECTION OF DOUBLE-STRANDED DNA

[75] Inventors: Alexander N. Glazer, Orinda; Scott C. Benson, Oakland, both of Calif.

[73] Assignee: The Regents of the University of California, Berkeley, Calif.

[ * ] Notice: This patent is subject to a terminal disclaimer.

[21] Appl. No.: 08/965,917

[22] Filed: Nov. 7, 1997

Related U.S. Application Data

[63] Continuation of application No. 08/708,666, Sep. 5, 1996, which is a continuation of application No. 08/161,231, Dec. 2, 1993, application No. 07/831,823, Feb. 6, 1992, abandoned, and application No. 07/493,347, Mar. 14, 1990, Pat. No. 5,138,501.

[51] Int. Cl.$^7$ .............................. C12Q 1/68; C07H 21/04
[52] U.S. Cl. ................................................. 435/6; 536/26.6
[58] Field of Search ................... 536/26.6, 22.1; 435/6

[56] References Cited

U.S. PATENT DOCUMENTS

| | | | |
|---|---|---|---|
| 4,116,521 | 9/1978 | Chirikjan | 439/274 |
| 4,737,454 | 4/1988 | Dattagupta et al. | 435/6 |
| 4,743,535 | 5/1988 | Carrico | 435/6 |
| 4,748,111 | 5/1988 | Dattagupta et al. | 435/6 |
| 5,312,921 | 5/1994 | Glazer et al. | 546/108 |
| 5,401,847 | 3/1995 | Glazer et al. | 546/107 |
| 5,565,554 | 10/1996 | Glazer et al. | 536/26.6 |
| 5,760,201 | 6/1998 | Glazer et al. | 536/22.1 |
| 5,783,687 | 7/1998 | Glazer et al. | 536/26.6 |

OTHER PUBLICATIONS

Wilson et al. J.Amer.Chem.Soc. 111:5008–5010, 1989.
Atwel, et al., *Am. Chem. Soc.* (1983) vol. 105:2913–2914.
Markovits, et al., *Biochemistry* (1983) vol. 22:3231–3237.
Markovits, et al., *Nucleic Acids Res.* (1985) vol. 13:3773–3788.
Munt, et al., *Biochemistry* (1985) vol. 24:1449–1460.
Wakelin, et al., *Med. Res. Revs* (1986) vol. 6:275–340.
Hopkins and Wilson, (1987) vol. 26:1347–1355.
Lauyaa, et al., *Biochemistry* (1985) vol. 24:5567–5575.
Nielsen, et al., *Biochemistry* (1988) vol. 27:67–73.
Delepierre, et al., *Biopolymers* (1984) vol. 28:2115–2142.
Angermoller and Soyavedaa–Soto, *Biotechniques* (1990) vol. 8:36–37.
Rosen and Villa–Komaroff, *Focus* (1990) vol. 12:23–24.
Hui, et al., *Nucleic Acids Res.* (1990) vol. 18:11099–1114.
Southern, *J. Mo. Biol.* (1975) vol. 98:503–517.
Sharp, et al., *Biochemistry* (1973) vol. 12:3055–3063.
Kroczek, *Nuc. Acids Res.* (1989) vol. 17:9997.
Maniatis, et al., *Molecular Cloning* (2nd ed. 1989) p.6–13.
*Biotechniques* (1990) vol. 8:36–38.
Gaugin, et al., *Biochemistry* (1978) vol. 17:5071–5078.
Gaugin, et al., *Biochemistry* (1978) vol. 17:5078–5088.
Markovits, et al., "Ethidium Dimer: A New Reagent for the Fluorimetric Determination of Nucleic Acids," *Analy. Biochem* (1979) vol. 94:259–264.
Markovits, et al., "Stable Fluorescent Complexes of Double–Stranded DNA with Bis–Intercalating Asymmetric Cyanine Dyes: Properties and Applications," *Nucleic Acid Res.* (1992) vol. 20(11):2803–2812.
Delaport, et al., *J. Med. Chem.* (1980) vol. 23:1336–1343.
Wright, et al., *Biochemistry* (1980) vol. 19:5825–5836.
Berman and Young, *Ann. Rev. Biophys. Biogen.* (1981) vol. 10:87–114.
Markovits, et al., "Ethidium Dimer: A New Reagent for the Fluorimetric Determination of Nucleic Acids," *Analytical Biochemistry* (1979) vol. 94:259–264.
Rye, et al., "Stable Fluorescent Complexes of Double–Stranded DNA with Bis–Intercalating Asymmetric Cyanine Dyes: Properties and Applications," *Nucleic Acids Research* (1992) vol. 20 (11):2803–2812.

*Primary Examiner*—Eggerton A. Campbell
*Attorney, Agent, or Firm*—Bozicevic, Field & Francis, LLP; Bret Field

[57] ABSTRACT

Novel fluorescent dyes are provided, characterized by having a fluorophore joined to a cationic chain. The dyes are found to provide for high enhancement upon binding to nucleic acid and have strong binding affinities to the nucleic acid, as compared to the fluorophore without the polycationic chain. The dyes find use in detection of dsDNA in gel electrophoresis and solution at substantially higher sensitivities using substantially less dye.

13 Claims, 10 Drawing Sheets

Table 1

| Structure | Dye | $t_{1/2}$ (min) | $F_{bound} / F_{free}$ |
|---|---|---|---|
| 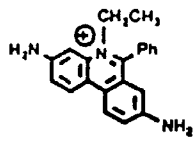 | Ethidium Bromide | 3.6 | 40 |
| 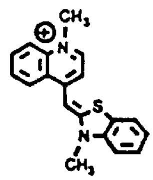 | Thiazole Orange | 4.3 | 2300 |
| 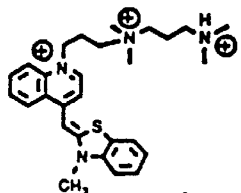 | Thiazole Orange Tetramethyl Propanediamine | 22 | 3800 |
| 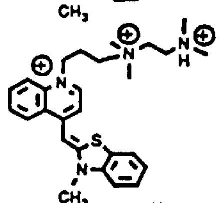 | Thiazole Orange Tetramethyl Ethanediamine | 26 | 3800 |
| 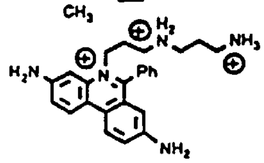 | Propanediamine Propidium | 31 | 40 |
| 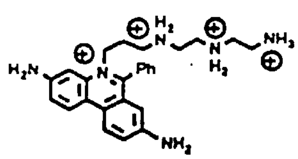 | Ethidium Diethylenetriamine | 75 | 30 |

Fig. 6

DYES DESIGNED FOR HIGH SENSITIVITY DETECTION OF DOUBLE-STRANDED DNA

This is a continuation of application Ser. No. 08/708,666 filed Sep. 5, 1996, which is a continuation of Ser. No. 08/161,231 filed Dec. 2, 1993, Ser. No. 07/831,823 filed Feb. 6, 1992, now abandoned, and Ser. No. 07/493,347 filed Mar. 14, 1990, now U.S. Pat. No. 5,138,501.

This invention was made with Government support under Grant Contract No. BE-FG-91ER61125 awarded by the Department of Energy. The Government has certain rights to this invention.

INTRODUCTION

1. Technical Field

The field of this invention is fluorescent dyes.

2. Background

The standard procedure for the detection of dsDNA on agarose or acrylamide gels, or in capillary electrophoresis, utilizes the phenanthridinium dye, ethidium bromide. In general, the detection on gels is accomplished in one of two ways. In one procedure, at the conclusion of gel electrophoresis, the gel is placed in an aqueous solution of ethidium bromide, allowed to equilibrate with the dye solution and is then transferred briefly to a dye-free solution to increase the amount of dye in the gel. The DNA-containing bands are then visualized by near-UV radiation on a transilluminator. In the second procedure, ethidium bromide at low concentration is incorporated into the running buffer for the electrophoretic separation and the visualization is performed as described above without further manipulation. The latter procedure is also employed for the detection of dsDNA components separated by capillary zone electrophoresis in systems that allow on-line fluorescence detection.

These commonly used procedures suffer from several disadvantages. High levels (0.5–2.5 $\mu$g/ml) amounts of ethidium bromide (a mutagen) are used. The detection involves the use of a UV-transilluminator. Consequently, the user is exposed to harmful near-UV radiation. The enhancement of fluorescence on binding ethidium bromide to dsDNA is approximately 35-fold and the dye binds relatively weakly to dsDNA ($K_{diss}=10^{-6}M^{-1}$). Consequently, the sensitivity of the dsDNA detection is low. Generally, the detection limit is about 1 ng of dsDNA in 1 mm×5 mm band on a gel.

An alternative dye has been recently reported, namely the asymmetric cyanine dye, thiazole orange (4-[3-methyl-2,3-dihydro-(benzo-1,3-thiazole)-2-ethylidene]-quinolinium iodide). While this dye shows many advantages over the ethidium bromide, nevertheless there is continuing interest in being able to provide for more sensitive techniques for detecting double-stranded nucleic acids in a sample, particularly where one is separating various fragments of the DNA and a fragment of interest may be present in extremely low concentration.

Relevant Literature

Lee et al. (1986) Cytometry 7: 508–517 report that thiazole orange, which has a 14-fold higher absorption coefficient than ethidium, bound to dsDNA with a fluorescence enhancement of about 3,000-fold. The dye was applied to the detection of reticulocytes (Lee et al. (1986), supra; and Lee and Chen (1989) U.S. Pat. No. 4,883,867) and bloodborne parasites (Lee and Mize (1990) U.S. Pat. No. 4,937,198). Rye et al. (1991) Nucleic Acids Res. 19: 327–333, showed that when thiazole orange at 0.05 $\mu$g/ml was added to the running buffer, DNA restriction fragments containing as little as 20 pg DNA-band could be readily detected with a laser-excited confocal fluorescence gel scanner (Quesada et al. (1991) Biotechniques 10: 616–625; Mathies and Huang (1992) Nature 359: 167–169). Inclusion of thiazole orange in the buffer in capillary zone electrophoresis allows detection of picogram amounts of dsDNA in the presence of $10^{-6}$–$10^{-7}$M free dye (Schwartz and Uhlfelder (1992) Anal. Chem. 64: 1737–1740.

SUMMARY OF THE INVENTION

Novel compositions and methods for their use are provided, where the compositions are fluorescent dyes providing high sensitivity for detection of double-stranded DNA (dsDNA) in solution or in gels. These compounds are characterized by the presence of a cationic chain, a high affinity for dsDNA as compared to available analogs, and a high fluorescence enhancement upon binding to dsDNA.

BRIEF DESCRIPTION OF THE FIGURES

FIG. 6 is Table 1, depicting the molecular structure, the molecular name, the $t_{1/2}$ as described on Page 16, line 4, while the $F_{bound}/F_{free}$ is a ratio of the fluorescence enhancement between the dye bound to DNA and the dye free in solution as described on page 14, lines 28ff.

DESCRIPTION OF THE SPECIFIC EMBODIMENTS

Figure 1:
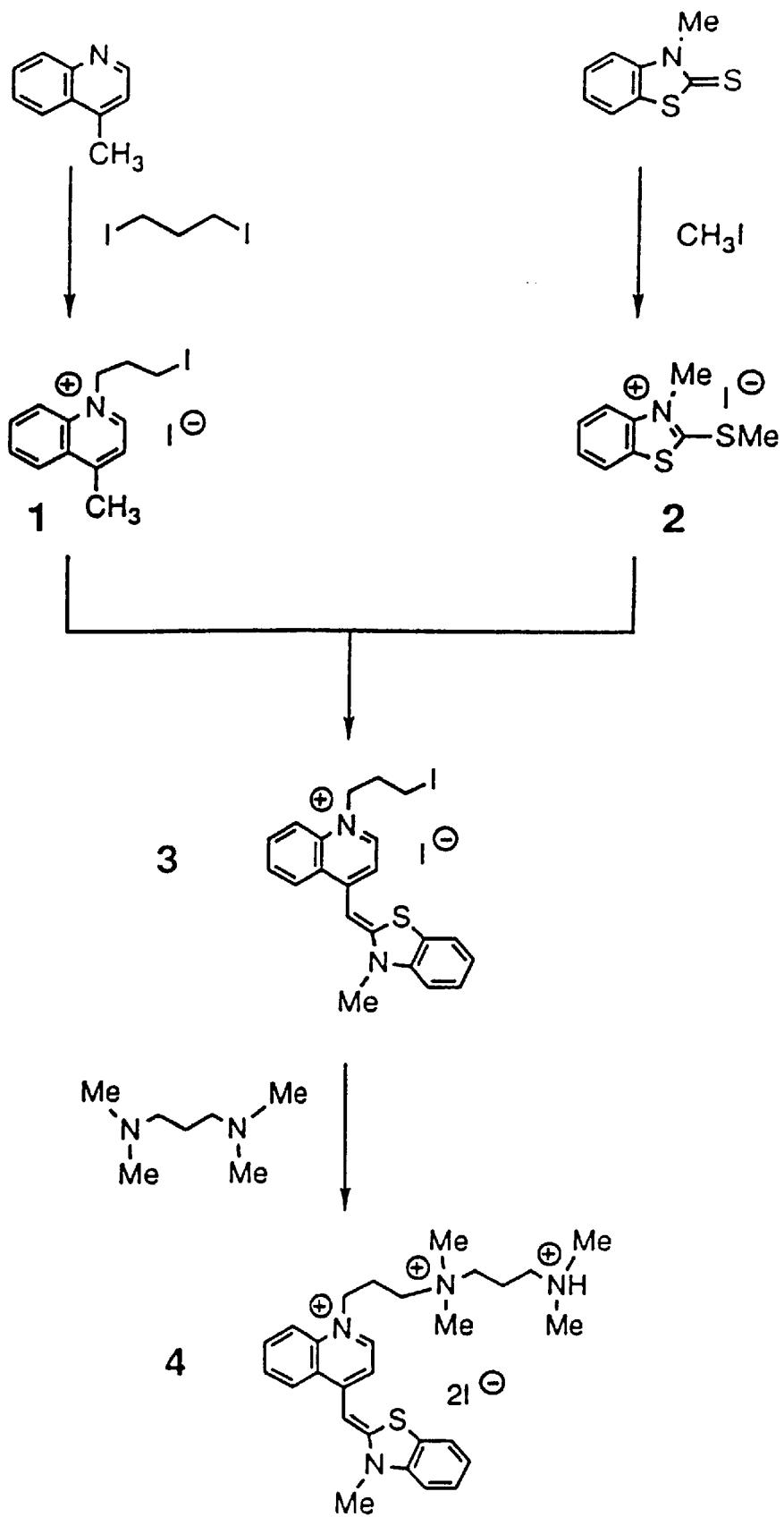
FIG. 1 is a scheme for the synthesis of N,N'-tetramethyl-1,3-diaminopropane thiazole orange.

In accordance with the subject invention, fluorescent dyes, particularly phenanthridinium and asymmetric cyanine polycationic dyes, are provided for detection of DNA in gels and in solution. In both cases, the subject dyes have a much higher binding affinity for dsDNA without loss of the fluorescence enhancement of the commercially available analogs. By virtue of the higher binding affinity, less dye need be used for binding to the dsDNA, and more extensive washing can be employed to remove the background dye, with subsequent lower loss of the dye which is intercalated in the dsDNA. In the case of the asymmetric cyanine derivatives, not only does one have the enhanced stability of the intercalated complex, but also one obtains an increased enhancement upon intercalation and ability to illuminate with green light, which eliminates the potential for hazardous UV exposure that is associated with the transilluminators now used for the detection of DNA on gels stained with ethidium bromide.

The subject dyes are characterized by having at least one cationic chain linked to an annular member, where the annular member will normally be carbon or nitrogen. The side chain will usually be aliphatic, having from 2 to 6 heteroatoms in the chain, particularly heteroatoms that provide for a positive charge, e.g. nitrogen and sulfur. The side chain will have at least one or two positive charges under the conditions in which the dye is used, and usually not more than five positive charges, more usually not more than about four positive charges. For the most part, the positive charges will be based on amino groups, although other elements which can support a positive charge, such as sulfur, phosphorus, iodine, to the extent that these cations are stable under the conditions of use, may also find application. The amino groups which are internal to the chain will be at least disubstituted and may be tri- or tetrasubstituted. The terminal amino group may be monosubstituted to tetrasubstituted. Normally, the nitrogens will be separated by at least two carbon atoms, although where heterocyclic groups are involved, such as piperazines, bipyridyl, or the like, the nitrogen atoms may be spaced by only one carbon atom, preferably at least two carbon atoms. The nitrogens may be substituted by any convenient group, usually of not more than about ten carbon atoms, more usually not more than about six carbon atoms, which may be alkyl, aryl, cycloalkyl, or with a heterocyclic group, or the nitrogen may be part of a heterocyclic ring. Preferably, alkylene amines will be employed, where the alkylene is of two to three carbon atoms, and the nitrogens, if substituted are substituted with lower alkyl groups of from 1–3 carbon atoms. For the most part, the side chain will be linear, with the sole branches being bonded to the heteroatoms in the chain.

The dyes which find use may be intercalating dyes or non-intercalating dyes where the binding is related to the opposite charges of the dye and the nucleic acid. The subject dyes will have a high binding affinity to nucleic acids, generally having two or more positive charges. The subject dyes will have an affinity for dsDNA of at least about $5 \times 10^6 M^{-1}$, more usually at least about $10^7 M^{-1}$, and may be greater than about $10^9 M^{-1}$, at ionic strengths of at least about 0.01, usually at least about 0.04, preferably at least about 0.2 at 25° C. It is observed that there is a substantial enhancement of fluorescence upon binding of the dye to the nucleic acid. Various dyes may find use, particularly monomeric dyes, such as ethidium bromide, thiazole orange, fluorescein, thiazole blue, acridine orange, and the like, and derivatives thereof. Of particular interest are those dyes which generally bind to nucleic acids, but intercalate into double-stranded nucleic acid.

The fluorophoric moieties may be cyclic, or polycyclic, particularly polycyclic aromatic having at least two rings, usually at least three rings and not more than about six rings, more usually not more than about five rings, where at least two of the rings are fused, usually at least three of rings are fused, and usually not more than four of the rings being fused. The aromatic compound may be carbocyclic or heterocyclic, particularly having from one to three, more usually one to two nitrogen atoms as heteroannular atoms. Other heteroannular atoms may include oxygen and sulfur (chalcogen).

The rings may be substituted by a wide variety of substituents, which substituents may include alkyl groups of from one to four carbon atoms, usually from one to two carbon atoms, oxy, which includes hydroxy, alkoxy and carboxy ester, generally of from one to four carbon atoms, amino, including mono- and disubstituted amino, particularly mono- and dialkyl amino, of from 0 to 8, usually 0 to 6 carbon atoms, thio, particularly alkylthio from 1 to 4, usually 1 to 2 carbon atoms, cyano, non-oxo-carbonyl, such as carboxy and derivatives thereof, particularly carboxamide or carboxyalkyl, of from 1 to 8 or 1 to 6 carbon atoms, usually 2 to 6 carbon atoms and more usually 2 to 4 carbon atoms, oxo-carbonyl or acyl, generally from 1 to 4 carbon atoms, halo, particularly of atomic number 9 to 35, etc.

Polycyclic compounds which find use include phenanthridines, acridines, porphyrins, phenylindoles, and bisbenzamides. Fluorophore moieties of particular interest will involve two ring systems, which are joined by a bond or a linking group having one or more ethylenic groups which are in conjugation with the aromatic moieties. Aromatic groups of interest include phenanthridine (benzquinoline), benzimidazole, benzthiazole, benzoxazole, quinoline, acridine and xanthine. Illustrative groups include thiazole orange, thiazole blue, ethidium, fluorescein, acridine, phenanthridine, xanthenes, and fluorones.

The side chain(s) may be linked to the fluorophore by any convenient means. Thus, the heteroatom of the side group may be used to substitute an active halogen or pseudohalogen, undergo reductive amination with a carbonyl group, be reacted with a carboxy group to form an amide, which, if desired, may then be reduced to a methylene amine, or the like. For other heteroatoms, analogous techniques may be employed, which find description in the literature.

Thus, the compounds can be prepared from alkylene polyamines, where the alkylene groups are of from 2 to 10, usually from 2 to 6 carbon atoms, and haloalkyl- or pseudohaloalkyl substituted fluorescent polycyclic aromatic compounds, e.g., phananthridines, acridines or asymmetric cyanines, which may be substituted or unsubstituted, to provide for ternary or quaternary amino groups. The amino groups may be quaternized with any convenient alkylation agent, either before or after reaction with the fluorescent compound or may be prepared initially as ternary amines using alkylamines, where the alkyl group will be from about 1 to 6, usually 1 to 3 carbon atoms. Illustrative of a compound would be N, N, N',N", N",-pentamethyl-N, N', N" -tris-(3,8-diamino-6-hydroxy-6-phenyl-5,6-dihydrophenanthridine). Other specific compounds of interest include: thiazole orange tetramethylpropane diamine ((N,N'-tetramethyl-1,3-diaminopropane)propyl thiazole orange), thiazole orange tetramethyl diamine, ethidium propane diamine, ethidium diethylene triamine, tetramethyldiaminopropane-propidium (TMP-2), tetramethyldiaminopropane-thiazole blue ((N,N'-tetramethyl-1,3-diaminopropane)propyl-TAB or tetramethyldiaminopropane-TAB), and triethylaminobutyl-thiazole blue (triethylaminobutyl-TAB).

The subject compounds find use as labeling agents, where the compounds are used in a process for detection of nucleic acid. Such applications include fluorescence in situ hybridization, flow cytometric analysis of cell populations, and the like.

The subject compositions find use in a variety of applications, including in separations employing an electrical field, e.g. electrophoresis. In employing the subject compounds, the nucleic acid, usually DNA, and the dye may be brought together in appropriately buffered medium and incubated for sufficient time for the dye to non-covalently bind and intercalate in the nucleic acid. The combined ratio of dye to double stranded nucleic acid may be varied widely ranging from about one molecule of dye per base pair to as little as one molecule of dye per 400 base pairs, or fewer, usually as few as one molecule of dye per 100 base pairs, depending upon the desired degree of sensitivity. Below about 15 bp/dye molecule, the increase in emission upon further addition of dye is not as efficient as above 15 bp/dye. Dye present in excess of one dye for four base pairs or more, may result in significant quenching, so that any increase in the amount of dye above a molar ratio of one dye molecule for four base pairs may not be desirable. However, the amount of dye combined with the DNA may be in a ratio of 1 per 2 base pairs or even 1 per 1 base pair or even greater ratios, where quenching is not observed. Generally, the amount of dye will range from about one molecule of intercalated dye for 4 to 100 base pairs, usually about 10 to 50 base pairs, for optimum results.

One may combine different samples with different dyes, followed by combining the different samples to be electrically separated. Thus, in the same channel, where an electrophoresis is carried out, one can detect the various bands with UV light, when appropriate, of the same wavelength, used for irradiation, by detecting the differences in fluorescent wavelength from the various bands.

The amount of nucleic acid will generally be conventional amounts employed for electrophoresis, generally ranging from about 5 pg/µl to 5 ng/µl. Because of the fluorescence efficiency, capillary electrophoresis can be performed efficiently. Various conventional buffers may be employed, such as tris-acetate or tris-borate, generally present in the range of about 1–50 mM, more usually in the range of about 1–20 mM, to provide a pH in the range of about 5–10, more usually about 7–9. Also, a metal ion chelator may be present in a minor amount, generally from about 0.05–0.5 mM. Conveniently, EDTA may be employed.

The dye and nucleic acid may be incubated, usually for at least about 5 minutes and not more than about 2 hours, where complex formation will normally be complete in less than about 1 hour, usually in about 30 min., at room temperature. The incubated solution may be used directly or further diluted, as appropriate, prior to application to the gel.

The electrophoresis may be performed in any convenient and conventional manner, where the bands may now be detected by fluorescence of the non-covalently bound and intercalated dye. The electrophoresis ensures that unbound dye is removed from the region of the bands and the dye is found to be retained in the nucleic acid, so that individual bands may readily be detected by fluorescence scanning.

Instead of incubating the nucleic acid with the dye prior to applying the nucleic acid to the gel, one may apply the dye after having carried out the separation. Since the intercalated dye will have a substantially different absorption-emission range (and much enhanced fluorescence intensity) from the unintercalated dye, one can readily detect the intercalated dye, even in the presence of significant amounts of the non-intercalated dye. Likewise, one may carry out the electrophoretic separation in the presence of a very low concentration of the dye in the gel and in the remaining buffer, substantially below about 0.2, particularly below about 0.1 µg/ml.

Any conventional detection system may be employed for detecting the individual bands. Depending on the particular dye employed, the excitation light will be chosen to be within a major absorption band of the absorbing dye.

Of particular interest is the use of a confocal laser scanning fluorescence imaging system. A system which has been found to be convenient employs a long-pass dichroic beam splitter to reflect the laser beam down through a microscope objective and onto the sample. The fluorescence emission is collected by the objective and passed through the beam splitter to a photodetector. The fluorescence emission is then passed through a spatial filter to effect confocal detection in a long-pass or band-pass color or interference filter before reaching a photomultiplier tube. An appropriate servomotor-driven XY translation stage is employed with a 2.5 µm resolution to translate the gel past the laser beam at a convenient speed, nearly about 1–5 cm/sec. A microcomputer may be employed to control the XY translation stage and to acquire and display images. The fluorescence images may then be pseudo-colored and coded to represent different intensity levels and contrast stretched with a histogram equalization method to enhance the images. To quantitate the image data, the image columns that enclose the nucleic acid bands may be extracted and integrated.

The nucleic acid may be readily isolated free of the intercalated fluorescent dye for further use. One may use the Geneclean® kit for recovery of 50% or better of the nucleic acid. By combining the intercalated dye containing nucleic acid with GLASSMILK™ in an aqueous solution of alkali metal iodide, e.g. 1–10 ng nucleic acid (1–5 µg/ml nucleic acid) and about 1–10 µg/ml of GLASSMILK™, incubating with agitation for about 5–60 mins. followed by centrifugation, the resulting pellet is isolated. After resuspending the pellet in an appropriate ethanolic buffered aqueous solution (e.g. 1:1) followed by centrifugation and repeating this washing procedure, the nucleic acid is obtained substantially free of the fluorescent dye.

By virtue of the use of the subject intercalating fluorescent dyes in the electrophoresis, greatly enhanced sensitivities are achieved due to the high level of fluorescence intensity which is obtained as well as the much lower background fluorescence. Sizes and amounts of DNA fragments in mixtures of unknown composition can be determined with a total amount of material ranging from 100 pg to 1 ng depending on the complexity of the mixture and the size range of the fragments. Thus, the subject method can find application in the detection of nucleic acid of less than about 5 ng, particularly less than about 1 ng, frequently less than about 100 pg, even less than about 20 pg.

Instead of employing the subject dyes for detection of nucleic acid bands in electrophoresis, compositions comprising dsDNA and the subject dyes at substantial saturation may be employed, where the dsDNA is joined to an entity for binding to another entity, either covalently or non-covalently. The entities will be either referred to as specific binding pairs, since the entities will have specific affinity for a complementary entity, as compared to diverse other types of molecules, or covalently binding functionalities for reacting with other molecules, such as polypeptides or saccharides.

Depending upon the fluorescence intensity one desires, one can vary the length of the dsDNA and the level of non-covalent binding and intercalation to increase the fluorescence intensity per molecule. Usually, there will be at least about 16 base pairs, more usually at least 20 base pairs, and one may have dsDNA of at least about 1 kbp or even 2 kbp or more. The particular length of the dsDNA is not critical to this invention and may be varied in accordance with the fluorescence intensity desired per molecule, purpose of the label, convenience, and the like.

The dsDNA should provide means for binding to another molecule. This can be achieved in a wide variety of ways, depending upon the manner in which the label is to be employed. For example, the dsDNA may include biotin conjugated nucleotides, one or more biotins, where the biotin will bind to avidin or streptavidin (hereinafter both will be referred to as "avidin"). The biotins may vary from one biotin per nucleotide to 0.1% of the nucleotides depending on the nature of the procedures, conditions, etc. Alteratively, any molecule may be employed, particularly a small organic molecule (less than about 2 kdal) which is unlikely to be encountered in the sample of interest, where the small organic molecule has a specific receptor or antibody, particularly monoclonal antibody, to which it specifically binds. Thus, thyroxine, corticosteroids, estrogens, retinoic acid, mannose and the like may be used with proteins which bind specifically to such molecules. Alternatively, synthetic molecules may be employed for which antibodies have been produced, such as 2,4-dinitrophenyl, barbiturate, phosphatidylcholine, etc. These molecules may be included during synthesis of the DNA by being linked to an internal or terminal nucleotide, where the DNA is synthesized in accordance with conventional automatic procedures, or may be added after synthesis of the DNA by linking to either available hydroxyl or amino groups.

The binding entity may be an active functionality for covalently bonding to a molecule having a functionality capable of forming a stable covalent link, such as amino, hydroxyl, thio, carboxyl, activated olefin or aryl, or the like where the functionality is other than a naturally occurring functionality of the nucleotide. The label may be modified with an activated olefin, such as maleyl, for reaction with a thiol group, a carboxyl for reaction with an amine, or the like. In this manner, many different types of molecules may be fluorescently labeled for use in diagnostics, both competitive assays and non-competitive assays, histology, cytology, separations e.g. electrophoresis, HPLC, FACS, and the like.

The strands of DNA may take various structures. In many situations, the dsDNA may comprise two strands, where the strands may be completely or only partially overlapping, where the ends may extend in the 5' and/or 3' directions, so that one strand may be substantially longer than the other strand, where the other strand may bind either 5' proximal, 3' proximal or centrally. Alternatively, the two strands may overlap to provide for staggered ends, where the single stranded portions of the DNA may then be used to bind to complementary sequences. Alternatively, one may provide a single strand with an inverted repeat, so that the strand loops back on itself to provide the double stranded portion. The hairpin structure may be used solely for labeling, or a single stranded portion of the hairpin may be employed for hybridizing to a complementary sequence. The hybridizing single stranded portion may be an extension at either the 5' or 3' end to provide for a staggered terminus or may be present in the loop of the hairpin.

The subject labels may be used in a wide variety of environments and contexts to provide for high levels of fluorescence intensity without interference from the molecules to which the labels bind, either directly or indirectly, the media employed, the conditions employed, and the like. Thus, the subject labels may be employed in specific binding pair assays, where the label may be readily linked to another molecule through a specific binding pair combination. For example, in diagnostic assays, one may combine an avidin conjugated antibody, where the antibody binds to a molecule of interest, to a biotin labeled DNA dye composition to provide for fluorescent labeled antibody.

Alternatively, the antibody may be labeled with biotin, so that avidin may act as a bridge between the biotin labeled antibody and the biotin labeled DNA dye composition. In this way, the fluorescent label may be added after combining the sample with a complementary specific binding pair member and carrying out the assay, followed by addition of label and removal of any nonspecifically bound label.

Where a single stranded DNA sequence is provided as part of the label, this can be used for hybridizing to complementary DNA or RNA sequences. The presence of the non-covalently bound and intercalated dye greatly enhances the stability of the dsDNA. Thus, one can introduce the subject labels into a denaturation medium under conditions where the non-covalently bound and intercalated dsDNA will be stable, while the sample DNA may be denatured to provide for single strands. Where single stranded DNA or RNA is present, there will be no need for providing for denaturation conditions. Therefore, the subject molecules may be used as probes to identify DNA sequences under a wide variety of conditions, including electrophoresis, polymerase chain reactions, where the single stranded sequence may serve as a primer, in Southern blotting, Northern blotting and the like.

The subject dyes may be preprepared with the single-stranded nucleic acid chain, so as to provide a composition where the dye is present and at least about 25% of saturation, and up to about 100% of saturation. Usually, the single-strand will be of at least about 50 bases, more usually at least about 100 bases, and may be a kb or more. By combining the dye with the single-stranded nucleic acid, particularly single-stranded DNA, a reagent is provided which can be used directly for detection of a sample comprising single-stranded DNA. The sample may be probed for a number of different sequences, by using different probes with different dyes, where the probe may be added concurrently or consecutively, preferably consecutively, washing away excess single-stranded probe and dye prior to the addition of the next dye.

One may also use the subject fluorescent non-covalently bound and intercalated DNA for in situ hybridization studies, intermolecular transfer of fluorescent molecules from one doubly stranded nucleic acid molecule to another, e.g. for transferring fluorescent dye without the fluorescer being transferred to the medium. This may find use in making chromosomes with triplex formation, in transferring to nucleic acid in a gel or on a membrane, etc. The fluorescer intercalated DNA may be bound to a particle, e.g. magnetic, to be removed after use as a transfer agent.

The subject compounds may be used with advantage with a confocal fluorescence imaging system, where less than 100 pg of DNA can be detected with some dyes while with other combinations, less than about 5 pg of DNA can be detected. In histology and cytology, the subject fluorescent labels provide for high sensitivity in detecting target epitopes, particularly at low levels.

For many applications, a plurality of fluorescent molecules will be desirable. Kits can be provided where the fluorescent molecules in the kit are characterized by having absorption maxima within a relatively narrow range, generally from about 460 to 540 nm, and emission maxima spaced apart by at least about 15 nm, preferably at least about 25 nm, usually not exceeding about 100 nm. As already indicated, reagents can be prepared, where the dye is combined with the nucleic acid probe and supplied in the container, for convenience, for use directly. Thus, the kits may have two or more containers containing different probes with different dyes, or two or more probes having the same dye, or combinations thereof. Alternatively, the probes in dyes may be maintained separately in separate containers.

The following examples are offered by way of illustration and not by way of limitation.

EXPERIMENTAL

I. Synthesis of (N,N'-tetramethyl-1,3-diaminopropane)propyl thiazole orange, diethylenetriamine ethidium, tetramethylethanediamine thiazole orange and propanediamine ethidium A. Synthesis of (N,N'-tetramethyl-1,3-diaminopropane) propyl thiazole orange.

Reactive cyanine dye intermediates were synthesized as outlined in FIG. 1. Compound 1 was produced in high yield by alkylation of lepidine with 5 equivalents of 1,3-diiodopropane in refluxing dioxane, while compound 2 was formed quantitatively when 3 equivalents of iodomethane were reacted with 3-methylbenzothiazole-2-thione in refluxing ethanol and precipitated with ether. Iodopropyl-lepidine 1 reacted in under 15 minutes with benzothiazole derivative 2 by the method of Brooker et al. ((1941) *J. Am. Chem. Soc.* 63: 3192–3203; Booker et al. (1942) ibid 64: 199–210) to produce the iodopropyl-thiazole orange derivative 3, in good yield. Compound 3 reacted with excess N,N'-tetramethyl-1, 3-diaminopropane to form (N,N'-tetramethyl-1,3-diamino propane)propyl-thiazole orange 4 in high yield.

Figure 2:
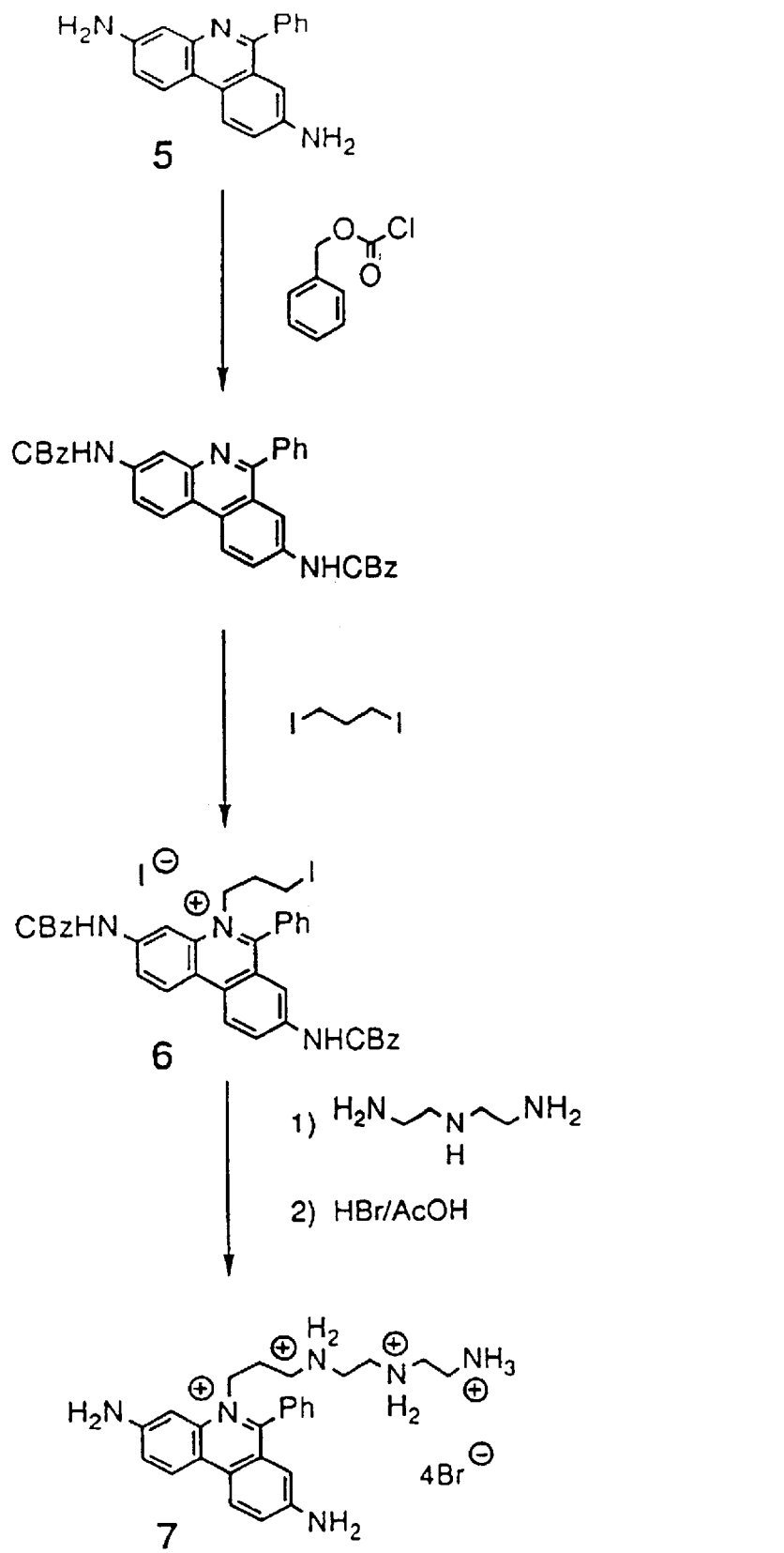
FIG. 2 is a scheme for the synthesis of diethylene triamine ethidium.

B. Synthesis of diethylenetriamine ethidium (FIG. 2)

The phenanthridinium derivative 5 was suspended in anhydrous pyridine. Carbobenzyloxychloride (2.2 equivalents) was added dropwise at 0° C., the reaction mixture stirred at room temperature for 12 hours, precipitated with ether/petroleum ether, the solid suspended in $CH_2Cl_2$ and washed with 10% $NaHCO_3$. The organic layer was dried with $MgSO_4$, concentrated, and purified by flash column $MeOH:CH_2Cl_2$ (1:50). The tan solid was suspended in anhydrous nitrobenzene, 5 equivalents 1,3-diiodopropane added. The mixture was heated at 160° C. in a sand bath for 4 hours, then 6 was precipitated with ether. Purification was with a flash column, $MeOH:CH_2Cl_2$ (1:10). Solid was suspended in anhydrous MeOH, and 10 equivalents 1,3-diethylenetriamine added. The mixture was refluxed for 7 hours. The product was precipitated with $H_2O$, the solid suspended in EtOH, acidified with concentrated HCl, and precipitated with ether. Purification was by flash column, $EtOAc:AcOH:H_2O$ (6:3:2, by volume). The carbobenzoxy groups were removed with HBr/AcOH to yield diethylenetriamine-ethidium, 7.

C. Tetramethylethanediamine thiazole orange and propanediamine ethidium

Tetramethylethanediamine thiazole orange and propanediamine ethidium were synthesized by procedures similar to those described above.

II. Properties of the dyes Synthesized in I.

The fluorescence enhancements of the ethidium dyes with polycationic chains were essentially the same as those for ethidium bromide. The same was true for the thiazole orange derivatives (Table I).

Figure 3:
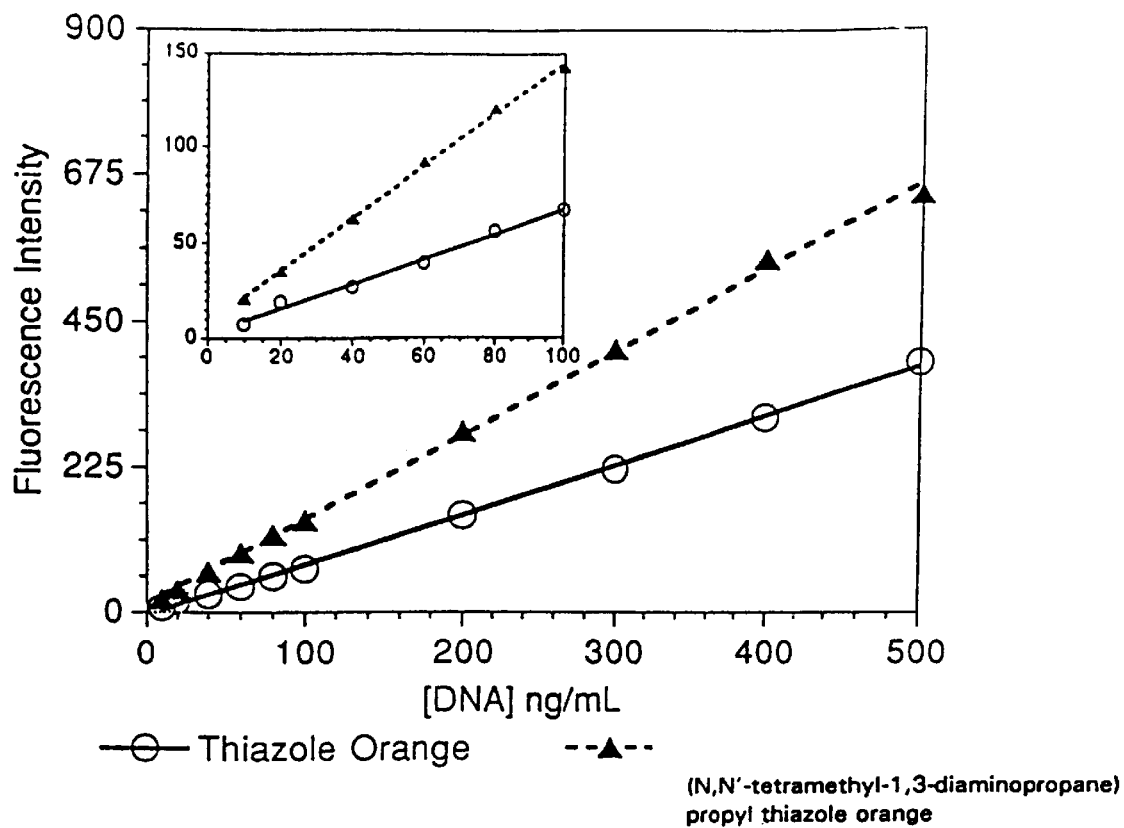
FIG. 3 is a graph showing the quantitation of calf thymus DNA in solution with thiazole orange and (N,N'-tetramethyl-1,3-diaminopropane)propyl thiazole orange.

Comparison of the titration of dsDNA in solution with thiazole orange and (N,N'-tetramethyl-1,3-diaminopropane) propyl thiazole orange, both at $7.9\times10^{-7}$M dye, is shown in FIG. 3.

Dye ($7.9\times10^{-7}$M) was added to DNA solutions (10–500 ng/ml) in 4 mM TAE buffer at pH 8.2 at room temperature. Excitation was at 488 nm and, for each dye, fluorescence was measured at emission maximum of its DNA complex. The inset shows the region of the titration curve from 10–100 ng DNA/ml in an expanded form.

With both (N,N'-tetramethyl-1,3-diaminopropane)propyl thiazole orange and thiazole orange, a linear dependence of fluorescence emission on dsDNA concentration was obtained from 10–500 ng dsDNA/ml. It should be noted that (N,N'-tetramethyl-1,3-diaminopropane)propyl thiazole orange gave a three-fold higher fluorescence signal than did thiazole orange. Moreover, the dsDNA determination could be readily extended to lower DNA concentrations with the former dye.

A. Rates of dissociation of the dsDNA-dye complexes and sensitivity of dsDNA detection on gels Electrophoresis was performed in a Mini-Protean II apparatus (BioRad, Richmond, Calif.) in 1 mm thick, vertical 0.9% agarose gels run at 10 V/cm in 40 mM Tris acetate—10 mM EDTA (TAE), pH 8.2. Gels were pre-electrophoresed for 1 hour prior to sample loading. Dye solutions were freshly prepared from concentrated stock dyes ($1\times10^{-4}$M in MeOH or DMSO), before each experiment by dilution into 4 mM TAE containing 50 mM NaCl, pH 8.2.

Figure 4:
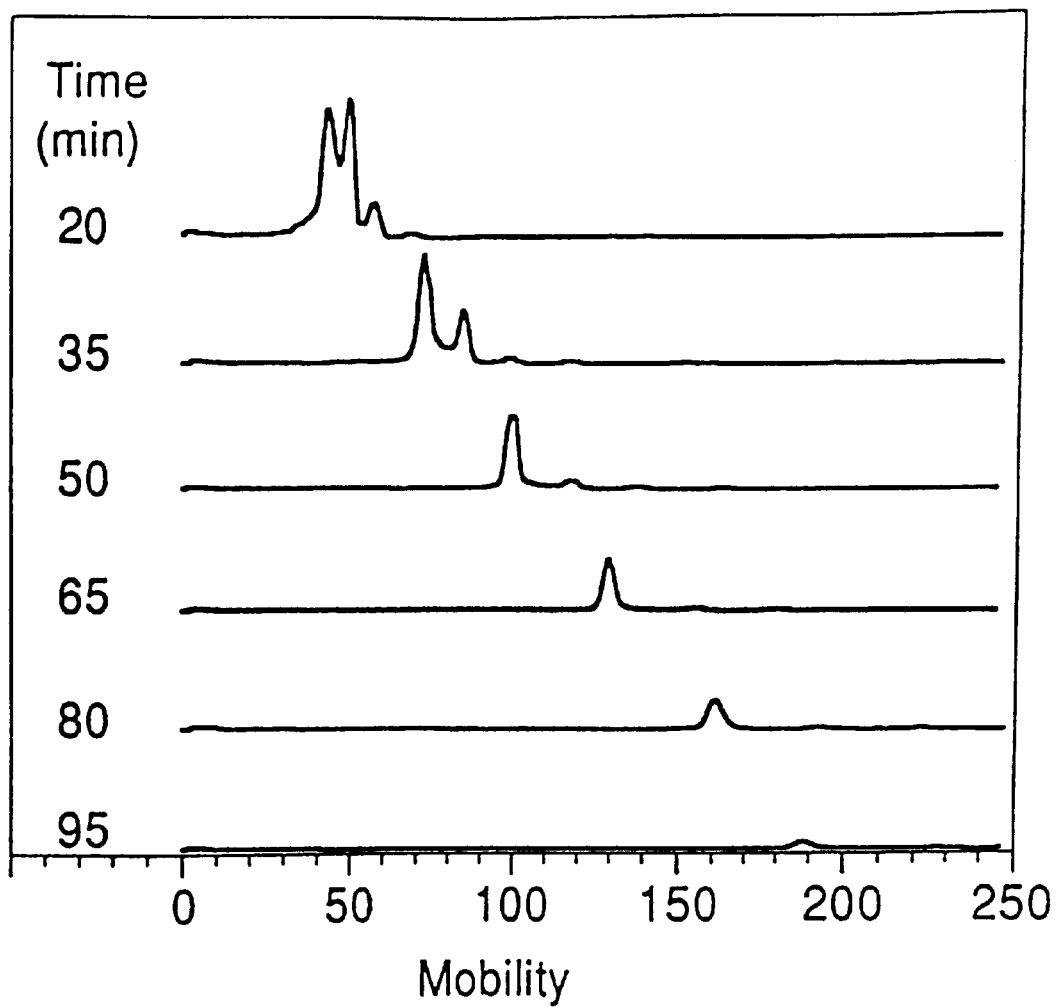
FIG. 4 is a graph of samples of a λ DNA/HindIII digest mixed with (N,N'-tetramethyl-1,3-diaminopropane)propyl thiazole orange at a DNA bp dye ratio of 5:1 in 4 mM TAE-80 mM NaCl, pH 8.2 electrophoresed on an agarose gel (0.9%) as described by Rye et al. (1991) Nucleic Acids Res. 19, 327–333, for the lengths of time indicated on the figure.
Figure 5A:
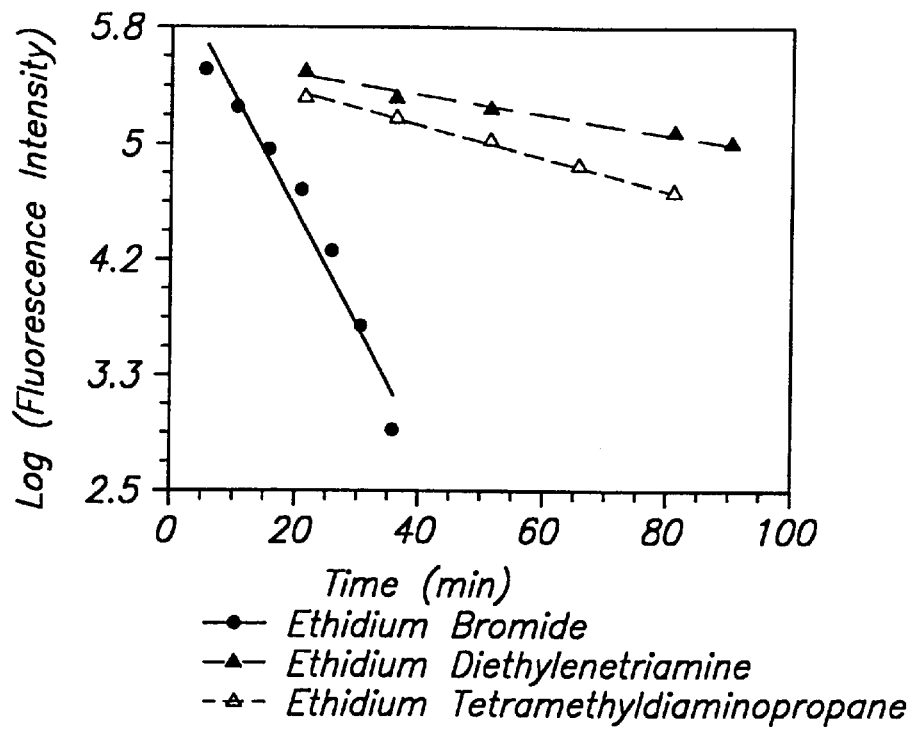
FIG. 5 is a comparison of the rates of dissociation of the various dsDNA-dye complexes under the conditions of electrophoresis described in relation to FIG. 4. Panel A compares the dissociation of dsDNA complexes with ethidium bromide, ethidium tetramethyldiaminopropane (tetramethyldiaminopropane-propidium (TMP-2)), and diethylenetriamine ethidium. Panel B compares the dissociation of dsDNA complexes with thiazole orange and (N,N'-tetramethyl-1,3-diaminopropane)propyl thiazole orange.
Figure 5B:
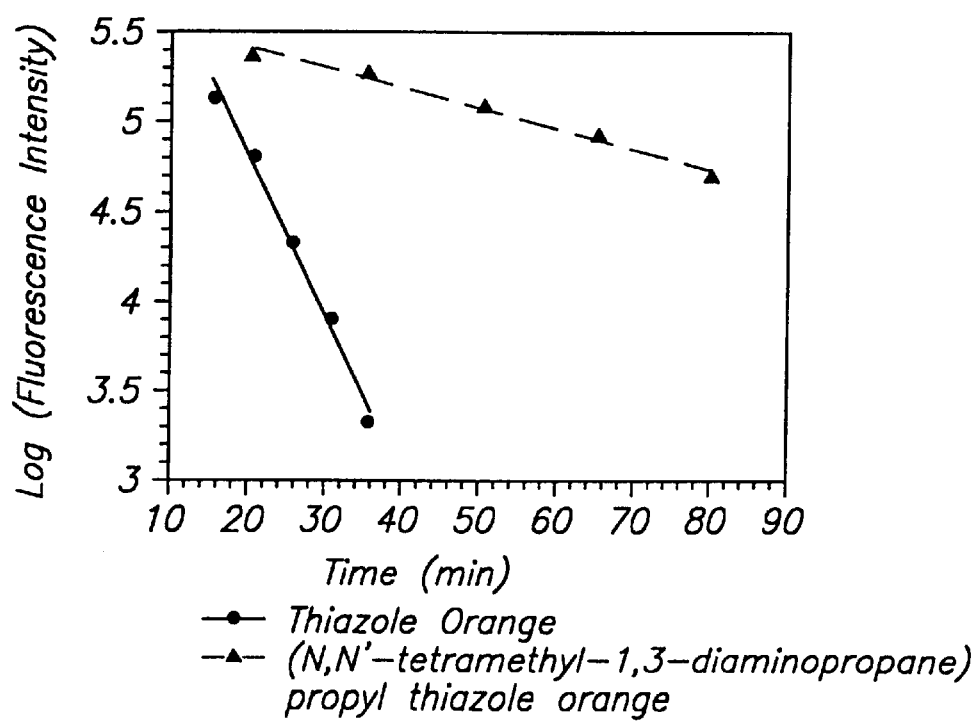
Figure 7:
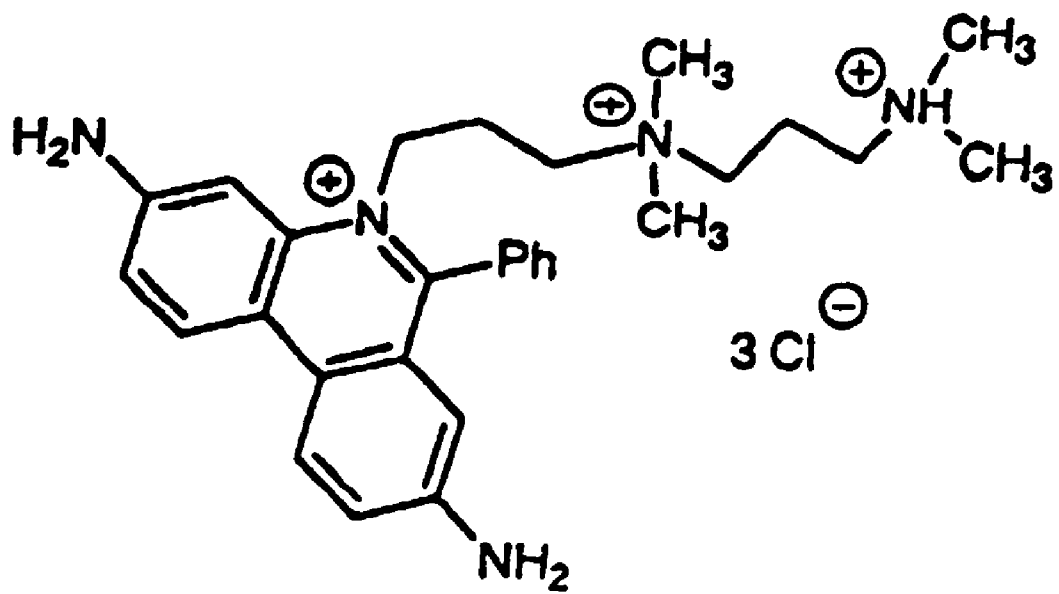
FIG. 7 shows the structure of tetramethyldiaminopropane-propidium (TMP-2).

The loss of the dyes on electrophoresis follows strict first order kinetics for ethidium bromide, thiazole orange, and derivatives with polycationic chains (FIGS. 4 and 5).

At the end of the electrophoresis, the gel was scanned with a laser-excited fluorescence gel scanner. Image processing was performed on each lane with Image™ software to obtain a fluorescence intensity plot for each time interval. The log plot of fluorescence intensity against time (see FIG. 5) indicates that the loss of dye follows first order kinetics and allows determination of the $t_{1/2}$ for the dissociation of the dsDNA-dye complex. For thiazole orange and ethidium bromide, 50 ng aliquots of plasmid M13 linearized with HindIII were mixed with the dye at DNA bp:dye of 2:1 in 4 mM TAE, pH 8.2, and applied to the gel at 5 min intervals. For the other dyes, 3 ng aliquots of ADNA/HindIII fragments were mixed with each dye at DNA bp:dye of 5:1 in 4 mM TAE-80 mM NaCl, pH 8.2, and loaded at 15 min intervals.

For the polycationic asymmetric cyanine derivatives, the dsDNA dye complexes are much more stable than those formed with thiazole orange, while they retain both the high extinction coefficient at about 500 nm and the high fluorescence enhancement on binding to dsDNA (>3000-fold). These new dyes thus allow post-staining of gels for dsDNA detection with 10-fold higher sensitivity than is attainable with thiazole orange and also permit more sensitive detection of dsDNA in solution. Moreover, efficient excitation of these dsDNA-dye complexes with green light eliminates the potential for hazardous UV exposure that is associated with the transilluminators now universally used for the detection of DNA on gels stained with ethidium bromide. These dyes find particular application with sensitive gel scanners that employ excitation in the visible region of the spectrum.

1. Determination of rates of dissociation of the dsDNA-dye complexes

The off-rates of the dye from dsDNA-dye complexes were measured by the following assay. λDNA/HindIII was mixed with each dye at a DNA base pairs-to-dye ratio of 2:1 for ethidium bromide and thiazole orange and 5:1 for the other dyes. Equal loads of the mixture were loaded on a gel at 5–15 min (as appropriate) time intervals in the course of electrophoresis. The amount of dye remaining in each band as a function of time of electrophoresis was determined by scanning with an argon ion laser-excited fluorescence gel scanner (Quesada et al. (1991) *Biotechniques* 10, 616–625; Mathies and Huang (1992) *Nature* 359, 167–169).

The relative stabilities of the complexes are conveniently assessed by comparing $t_{1/2}$ values (Table I in FIG. 6). It is evident from this comparison that the dyes bearing the polycationic substituents bind much more strongly to dsDNA.

2. Comparison of the sensitivity of detection by post-staining with different dyes Samples containing amounts varying from 5 to 30 ng of λ DNA/HindIII fragments were electrophoresed in duplicate sets on the same gel. After 45 minutes of electrophoresis, the gels were cut in half and stained in 40 mM TAE buffer. One half of a gel was soaked in (N,N'-tetramethyl-1,3-diaminopropane)propyl thiazole orange ($2 \times 10^{-8}$M) and the other half in thiazole orange ($2 \times 10^{-7}$M). One half of a second gel was soaked in diethylenetriamine ethidium ($2 \times 10^{-7}$M) and the other half in ethidium ($2 \times 10^{-6}$M), all in 40 mM TAE. After soaking for 40 min, the gels were transferred for 20 min to a dye-free 40 mM TAE solution and then scanned as described above.

As anticipated from these results, post-staining of gels with (N,N'-tetramethyl-1,3-diaminopropane)propyl thiazole orange at a concentration 10-fold ($2 \times 10^{-8}$M) lower than with thiazole orange ($2 \times 10^{-7}$M) gave 14-fold more sensitive detection of dsDNA. Post-staining with diethylenetriamine ethidium at a concentration 10-fold lower ($2 \times 10^{-7}$M) than with ethidium bromide ($2 \times 10^{-4}$M) gave 1.7-fold higher sensitivity of dsDNA detection.

III. Synthesis and Properties of Three Additional Polycationic Dyes.

The following three dyes were synthesized and found suitable for use in the high sensitivity detection of nucleic acids in solutions and on gels. The three dyes are tetramethyldiaminopropane-propidium (TMP-2); tetramethyldiaminopropane-thiazole blue (tetramethyldiaminopropane-TAB or (N,N'-tetramethyl-1,3-diaminopropane)propyl-TAB), and triethylaminobutyl-thiazole blue (triethylaminobutyl-TAB). It was found that with each of the above three dyes, the dyes formed more stable complexes with nucleic acids than did dyes lacking a cationic chain and provided for a high fluorescence enhancement upon dye-nucleic acid complex formation.

A. Synthesis of TMP-2 (Tetramethyldiaminopropane-propidium)

TMP-2 was prepared as in Benson et al., Nucleic Acids Research (1993) 21: 5727–5735. Ethidium bromide was suspended in anhydrous pyridine. To the suspension was added dropwise 2.2 equivalents carbobenzyloxychloride at 0° C. The mixture was then stirred for 12 hours at room temperature, and the product was precipitated with ether/petroleum ether. The precipitated solid product was then suspended in $CH_2Cl_2$ and washed with 10% $NaHCO_3$. The organic layer was dried with $MgSO_4$ and the product purified by flash column chromatography ($MeOH:CH_2Cl_2$ (1:50)). The purified product was recrystalized in $CH_2Cl_2$/ether. The resultant tan solid was suspended in anhydrous nitrobenzene, to which 5 equivalents of 1,3-diiodopropane were added. The suspension was then heated to 160° C. in a sand bath for 4 hours, the product was precipitated with ether and purified by flash column ($MeOH:CH_2Cl_2$ (1:10)). The product was then suspended in anhydrous MeOH, to which 10 equivalents of N,N'-tetramethyl-1,3-diaminopropane were added. The mixture was refluxed for 7 hours, and the product was precipitated with $H_2O$. The resultant solids were suspended in EtOH and acidified with concentrated HCl, from which the product was precipitated with ether and purified by flash column, $EtOAc:AcOH:H_2O$ (6:3:2). Finally, the dicarbobenzyloxy protecting groups were removed with HBr/AcOH to yield TMP-2.

TMP-2 was observed to bind to dsDNA with a 40-fold fluorescence enhancement similar to that of the commonly used phenanthridium dye, ethidium bromide. The absorption maximum of the dsDNA-bound dye was found to be at 529 nm and the fluorescence emission maximum was found to be at 612 nm. However, the complex that TMP-2 forms with dsDNA is much more stable than the complex formed by ethidium bromide. The half-time ($t_{1/2}$) for the dissociation of the preformed dye-dsDNA complex on electrophoresis on agarose gels at room temperature in 40 mM Tris-acetate, 1 mM EDTA, pH 8.2 (TAE buffer) at a DNA basepairs:dye ratio of 20:1 is 3.6 min for ethidium bromide (see Benson et al., Nucleic Acids Research (1993) 21:5720–5726) but was found to be 50 min for TMP-2.

Because of the superior stability of the TMP-2 complex with DNA, TMP-2 can be used at a twenty fold lower concentration than ethidium bromide for quantitation of nucleic acids in solution or by post-staining of gels. The lower background allows at least ten-fold more sensitive DNA detection.

B. Synthesis of (N N'-tetramethyl-1,3-diaminopropane) propyl-TAB

Figure 8:
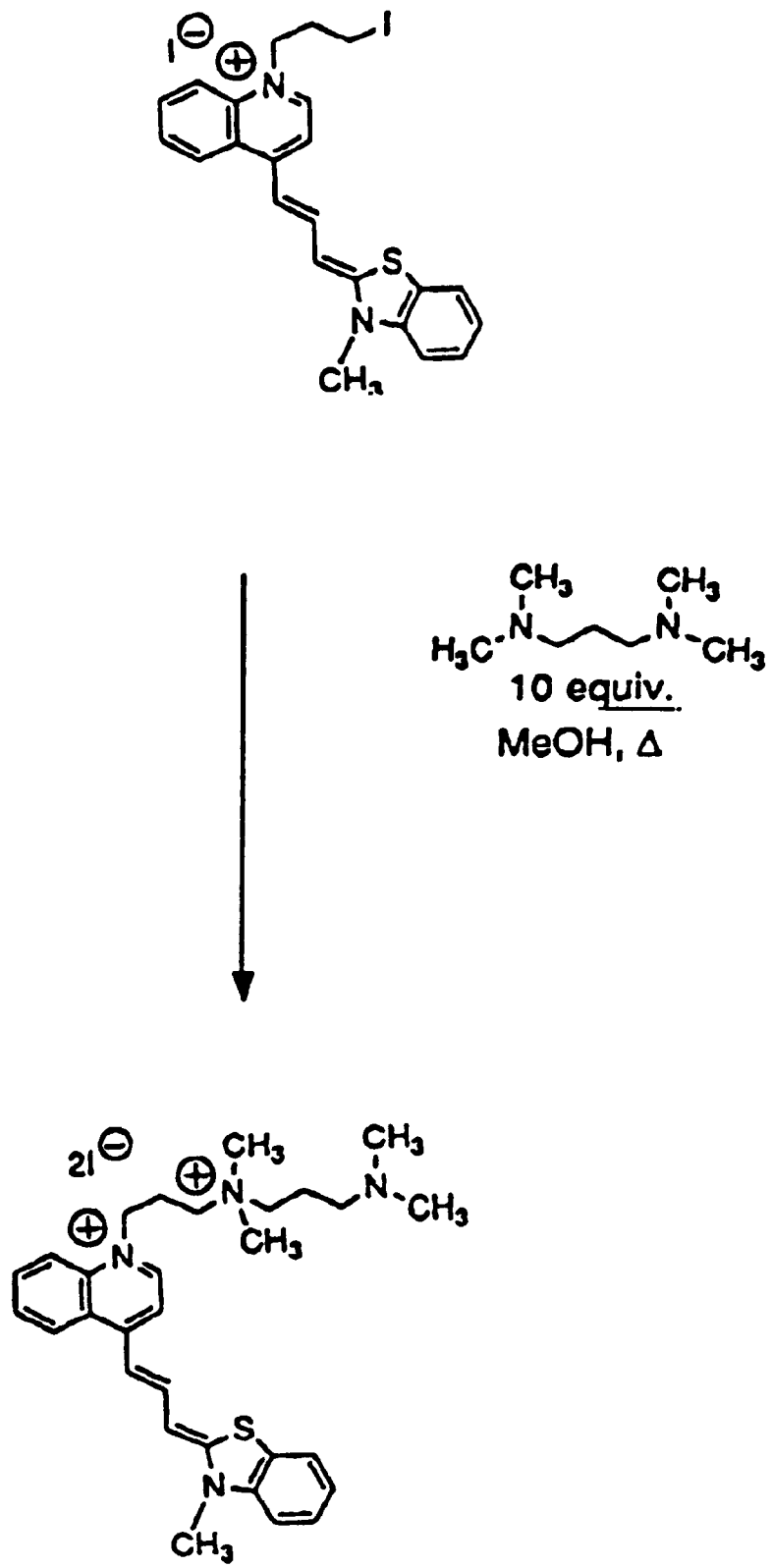
FIG. 8 is a scheme for the synthesis of (N,N'-tetramethyl-1,3-diaminopropane)propyl-TAB.

The scheme for the synthesis of tetramethyldiaminopropane-TAB ((N,N'-tetramethyl-1,3-diaminopropane)propyl-TAB) is provided in FIG. 8. Iodopropane-TAB is synthesized as described in Benson et al., Nucleic Acids Research (1993) 21:5727–5735. The iodopropane-TAB is suspended in anhydrous MeOH, 10 equivalents of N,N'-tetramethyl-1,3-propanediamine were added, and the mixture was refluxed for 6 hrs. The product was precipitated with ether and purified on a flash column in $EtOAc:AcOH:H_2O$ (1:2:2 by volume) to give (N,N'-tetramethyl-1,3-diaminopropane)propyl-TAB in 70% yield.

This dye was found to have an absorption maximum at 635 nm (methanol) with an $\epsilon \sim 150{,}000$ $M^{-1}$ $cm^{-1}$. The dye showed a large fluorescence enhancement on binding to nucleic acids and the DNA-dye complex could be efficiently excited at either 633 nm (He-Ne laser) or 647 nm (Ar—Kr—laser). The dsDNA:dye complex emitted at 662 nm. Post-staining of gels provided for the ready detection of 25 picograms of dsDNA. This sensitivity is similar to the best sensitivity reported for fluorescence detection of DNA on post-stained gels.

C. Synthesis of triethylaminobutyl-TAB

Figure 9:
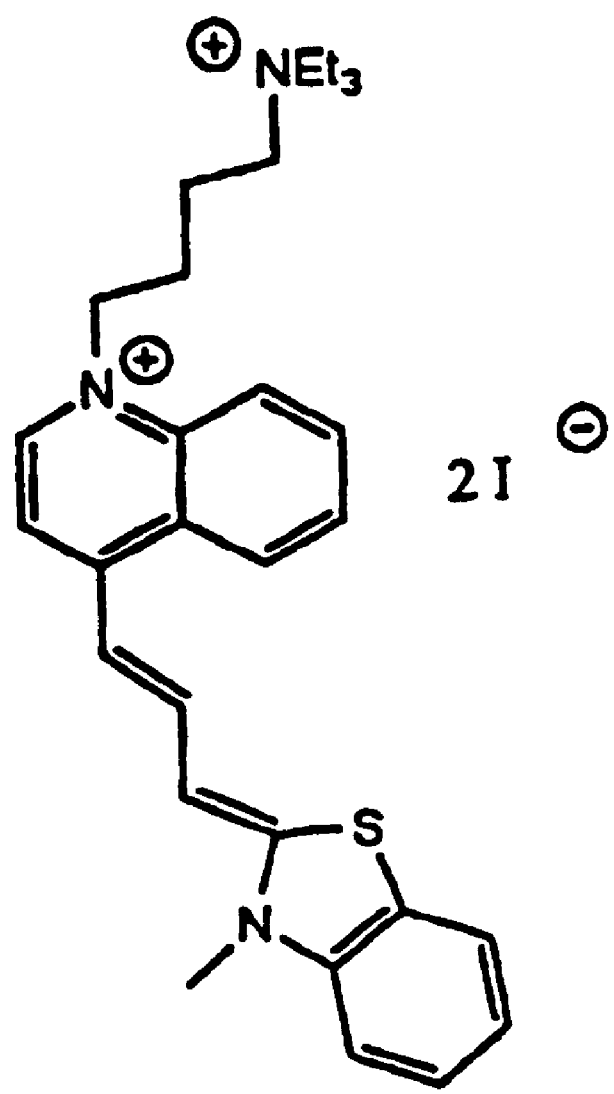
FIG. 9 shows the structure of triethylaminobutyl-TAB.

Iodobutyl-TAB was synthesized as previously described in Benson et al., Nucleic Acids Research (1995) 231:247–255. Iodobutyl-TAB (100 mg) was dissolved in absolute EtOH (15 ml) and dry triethylamine was added (0.5 ml). The mixture was refluxed for 3 hrs and then dried by rotary evaporation. The crude triethylaminobutyl-TAB (FIG. 9) was recrystallize from $CH_2Cl_2$/MeOH (9:1 by volume)-petroleum ether in a yield of approximately 80%.

Figure 10:
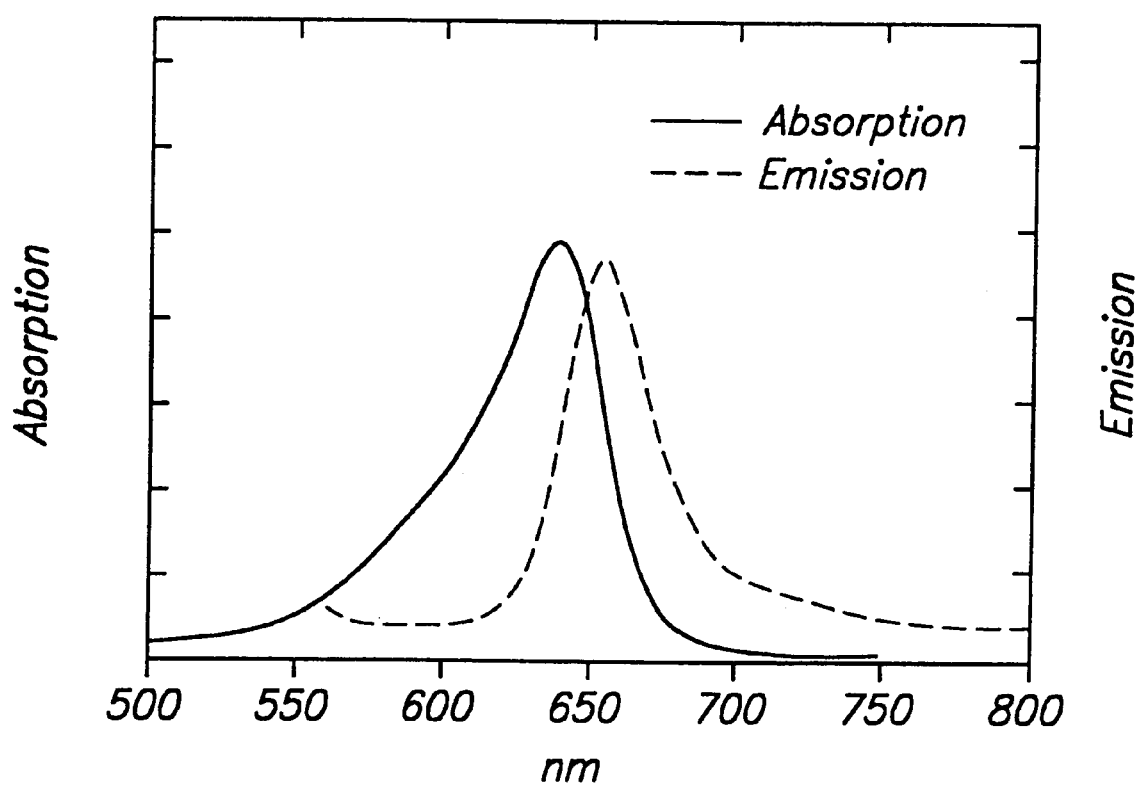
FIG. 10 shows the absorbance and emission spectra of calf-thymus dsDNA-triethylaminobutyl-TAB complex at DNA base pairs:dye ratio of 20:1 in 40 mM TAE buffer pH 8.2, where the absorbance spectrum was recorded at $10^{-6}$M dye and the emission spectrum was recorded at $10^{-7}$M dye with excitation at 550 nm.

The resultant dye was found to have a molar absorbance coefficient at 633 nm in MeOH of 160,500 $M^{-1}$ $cm^{-1}$, at 628 nm of 64,400 $M^{-1}$ $cm^{-1}$ in TAE buffer, and at 639 nm of 61,200 $M^{-1}$ $cm^{-1}$ when complexed to dsDNA at a DNA basepairs:dye ratio of 20:1. The fluorescence emission maximum of the DNA-bound dye was found to be at 652 nm. (FIG. 10).

Triethylaminobutyl-TAB was used to post-stain DNA restriction fragments separated by electrophoresis on agarose gels. A λ DNA/HindIII digest (1 ng) was fractionated by electrophoresis on a 0.9% agarose gel in 40 mM TAE for 60 min. at 10 V/cm at room temperature. Post-staining was performed with triethylaminobutyl-TAB in 40 mM TAE for 20 min at concentrations ranging from $10^{-7}$ to $10^{-9}$M. The gel was destained for 20 min in the 40 mM TAE buffer and the bands were detected by scanning with a confocal laser-excited fluorescence gel scanner (Mathies et al., Rev. Sci. Instrum. (1994) 65:807–812) equipped with an argon-krypton laser. With excitation at 647 nm, bands with 20 pg of DNA were detected.

It is evident from the above results that the subject compositions provide a new and important class of DNA binding fluorescers. These compositions provide for enhanced fluorescence, showing enhanced binding of the fluorescer where the half times under electrophoretic conditions are substantially enhanced in comparison to the generally available analogs. The equilibrium between free dye and dye bound to the DNA is greatly favored as to bound dye as compared to the analogs without the polycationic side chains. Thus, one can detect much lower amounts of DNA, using less of the dye and having much lower backgrounds to provide for more sensitive and more accurate detection of DNA. For the polycationic phenanthridine derivatives, the advantage of tighter binding is that staining of gels (detection of DNA and solution) can be accomplished with 10-fold less dye than with ethidium bromide. Moreover, more extensive washing of the gel after staining is possible with much less loss of bound dye, which translates to a 10-fold improvement in the sensitivity of dsDNA detection. The red-emitting dyes provide a number of advantages, as excitation in the red region of the spectrum is particularly favorable because it minimizes autofluorescence from chromophores commonly found in biological systems (such as flavins and prophyrins), the Raman scattering of water, and fluorescence contributions from plastics and other materials.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A polycationic fluorescent compound consisting of a polycyclic aromatic fluorophore having at least two rings and a positively charged side chain, wherein said side chain has at least two positive charges.

2. The fluorescent compound according to claim 1, wherein said fluorophore comprises at least 3 rings and not more than 6 rings, wherein at least two of said rings are fused.

3. The fluorescent compound according to claim 1, wherein said fluorophore is heterocyclic and has from one to two nitrogen atoms as annular atoms.

4. The fluorescent compound according to claim 1, wherein said compound has an affinity for dsDNA of at least about $5\times10^6 M^{-1}$.

5. A fluorescent compound prepared from a fluorescent polycyclic aromatic compound and an alkylene polyamine, wherein said fluorescent compound comprises a side chain having at least two positive charges.

6. The fluorescent compound according to claim 5, wherein said fluorescent polycyclic aromatic compound is a phenanthridine.

7. The fluorescent compound according to claim 5, wherein the alkylene group of said alkylene polyamine is from 2 to 10 carbon atoms.

8. The compound according to claim 5, wherein the amino groups of said alkylene polyamine are substituted with alkyl groups of from 1 to 3 carbon atoms.

9. The fluorescent compound according to claim 5, wherein said fluorescent polycyclic aromatic compound is an acridine.

10. The fluorescent compound according to claim 9, wherein the alkylene group of said alkylene polyamine is from 2 to 10 carbon atoms.

11. The compound according to claim 9, wherein the amino groups of said alkylene polyamine are substituted with alkyl groups of from 1 to 3 carbon atoms.

12. A fluorescent compound prepared from a phenanthridine and an alkylene polyamine of from 2 to 6 carbon atoms, wherein the amino groups of said alkylene polyamine are substituted with alkyl groups of from 1 to 3 carbon atoms.

13. A fluorescent compound prepared from an asymmetric cyanine and an alkylene amine of from 2 to 6 carbon atoms, wherein the amino groups of said alkylene amine are substituted with alkyl groups of from 1 to 3 carbon atoms.

* * * * *